US009272062B1

(12) United States Patent
Heflin, III et al.

(10) Patent No.: US 9,272,062 B1
(45) Date of Patent: Mar. 1, 2016

(54) AIR FRESHENER AND ORNAMENT

(71) Applicant: Brandywine Product Group International Inc., Wilmington, DE (US)

(72) Inventors: Robert H. Heflin, III, Hockessin (DE); Kyle Brandenburg, Middletown, DE (US)

(73) Assignee: Brandywine Product Group International Inc., Wilmington, DE (US)

( * ) Notice: Subject to any disclaimer, the term of this patent is extended or adjusted under 35 U.S.C. 154(b) by 437 days.

(21) Appl. No.: 13/726,687

(22) Filed: Dec. 26, 2012

(51) Int. Cl.
*A61L 9/04* (2006.01)
*A61L 9/12* (2006.01)

(52) U.S. Cl.
CPC ........................................ *A61L 9/12* (2013.01)

(58) Field of Classification Search
CPC ............. A61L 9/04; A61L 9/042; A61L 9/12; A01M 1/2055; Y10S 261/88; Y10S 428/905
USPC ............ 239/60, 36, 34, 200, 47, 51.5, 55, 57; 40/317, 661; 446/73, 77, 424, 425
See application file for complete search history.

(56) References Cited

U.S. PATENT DOCUMENTS

| | | | | |
|---|---|---|---|---|
| 2,734,769 A * | 2/1956 | Holz | ................... | A01M 1/2055 239/57 |
| 4,419,395 A * | 12/1983 | Sugimoto | ............ | A44C 15/002 239/36 |
| 4,476,171 A * | 10/1984 | Takeuchi | ................ | A61L 9/042 156/63 |
| 5,437,410 A * | 8/1995 | Babasade | ................ | A61L 9/042 206/0.7 |
| 5,865,372 A * | 2/1999 | Ceresko | .................... | A61L 9/03 239/60 |
| D594,953 S * | 6/2009 | King et al. | .................... | D23/366 |
| 7,887,760 B2 * | 2/2011 | Yamamoto | .......... | A01M 1/2033 422/124 |
| D714,924 S * | 10/2014 | Brandenburg | ............... | D23/367 |
| D722,154 S * | 2/2015 | Muller | ........................ | D23/368 |
| 2006/0000920 A1 * | 1/2006 | Leonard | .................... | A61L 9/12 239/34 |
| 2007/0262166 A1 * | 11/2007 | Majerowski | ........ | A01M 1/2055 239/57 |
| 2008/0179424 A1 * | 7/2008 | Cheung | ..................... | A61L 9/03 239/60 |
| 2008/0245890 A1 * | 10/2008 | Lockwood | .......... | A01M 1/2055 239/60 |
| 2008/0313795 A1 * | 12/2008 | Lu | ............................. | A61L 9/05 4/231 |
| 2009/0235443 A1 * | 9/2009 | Arora | ........................ | A61L 9/05 4/231 |
| 2010/0192291 A1 * | 8/2010 | Burt | ........................ | E03D 9/007 4/223 |
| 2010/0212074 A1 * | 8/2010 | Burt | ........................ | E03D 9/007 4/231 |

\* cited by examiner

*Primary Examiner* — Arthur O Hall
*Assistant Examiner* — Joseph A Greenlund
(74) *Attorney, Agent, or Firm* — Panitch Schwarze Belisario & Nadel LLP

(57) ABSTRACT

A combination air freshener and ornament has an ornament body and a support stand that serves dual purpose as a hanging hook when the ornament is in a hanging configuration and as a support stand when the ornament is in a standing display configuration. The support stand optionally has plugs at each end that removably engage with a receiving hole in the ornament body. The ornament body and/or the support stand are formed of fragranced polymer. One embodiment forms the ornament body in a gingerbread man configuration and the support stand in a candy cane configuration.

15 Claims, 16 Drawing Sheets

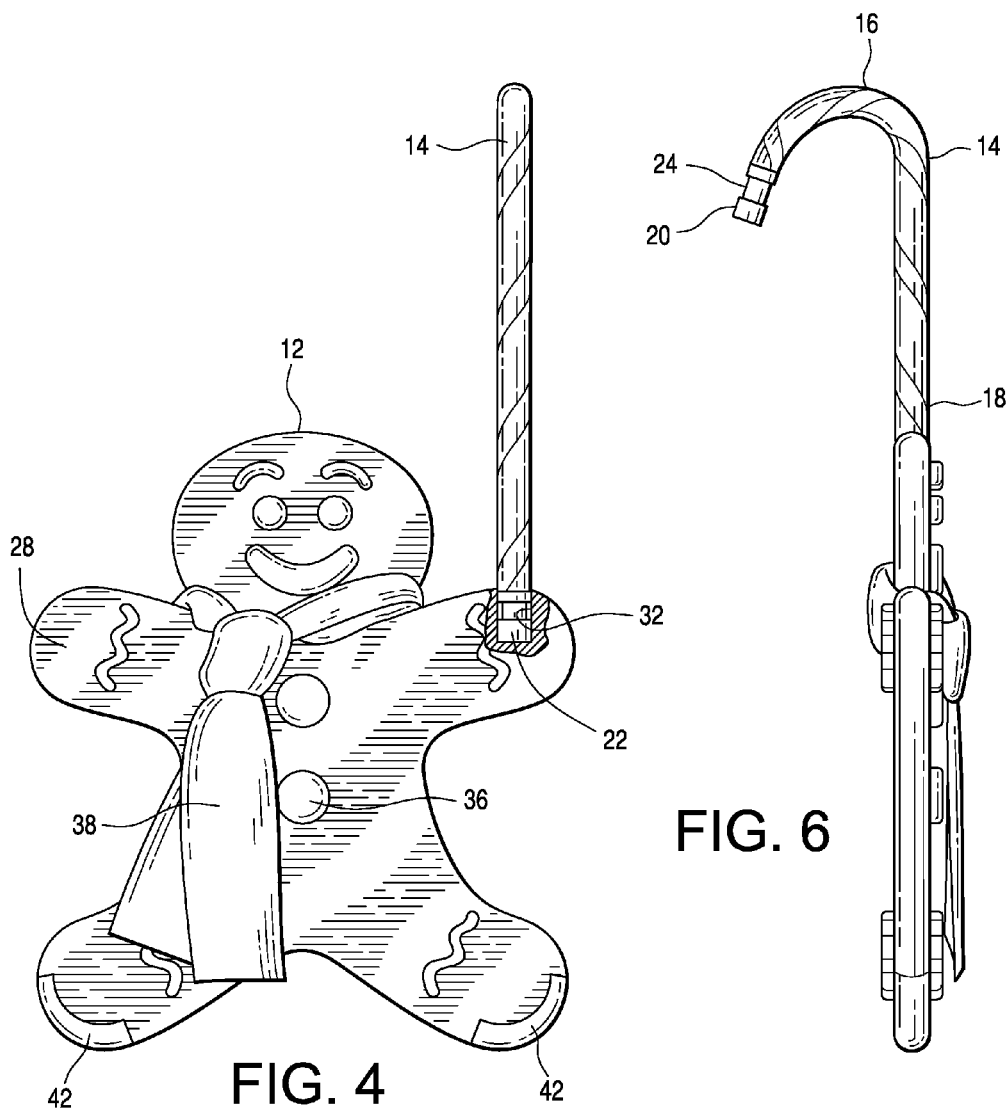
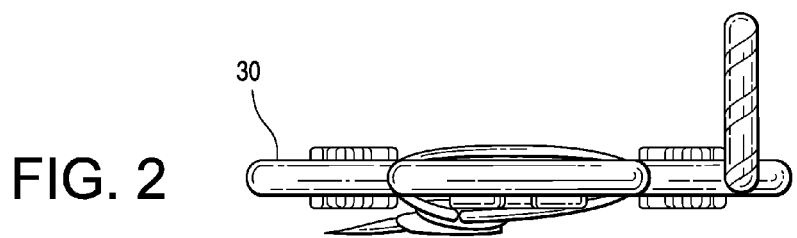

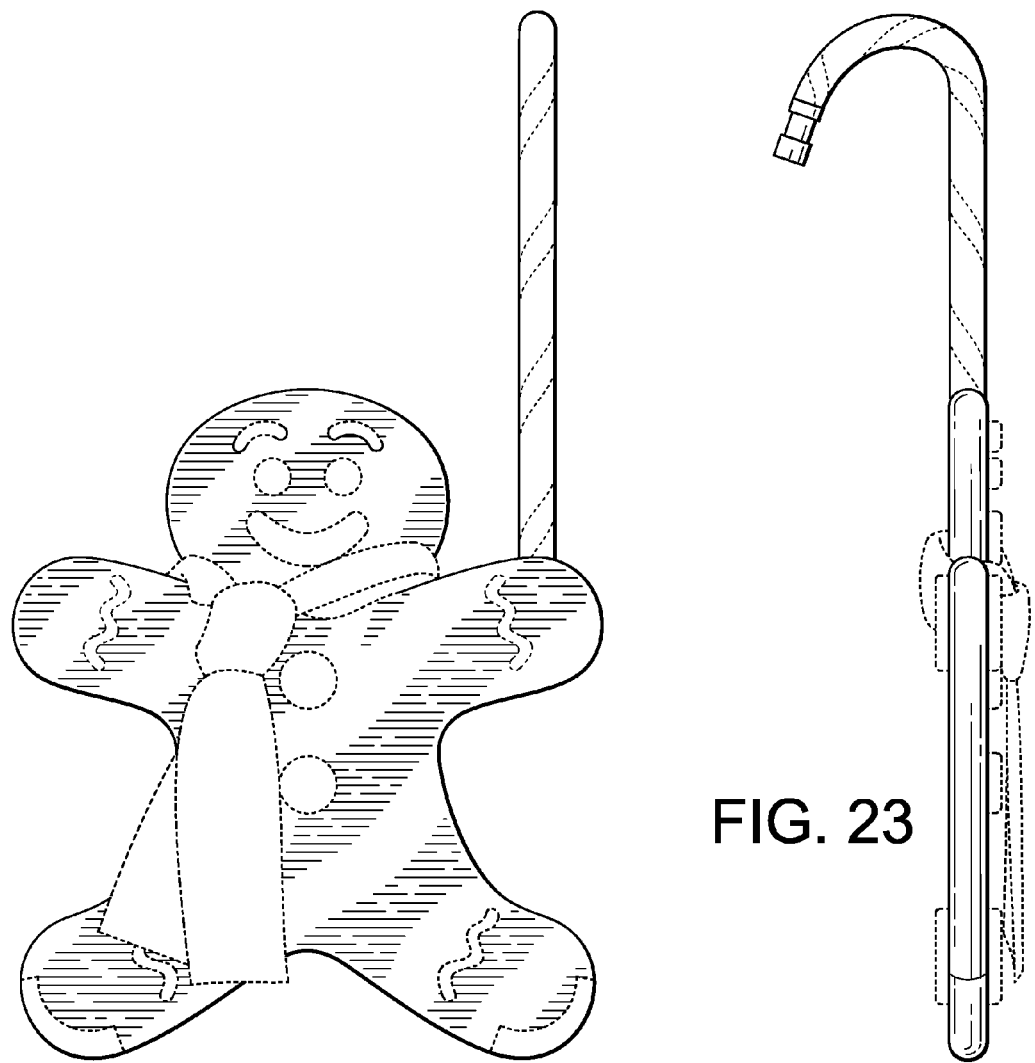
FIG. 23
FIG. 21
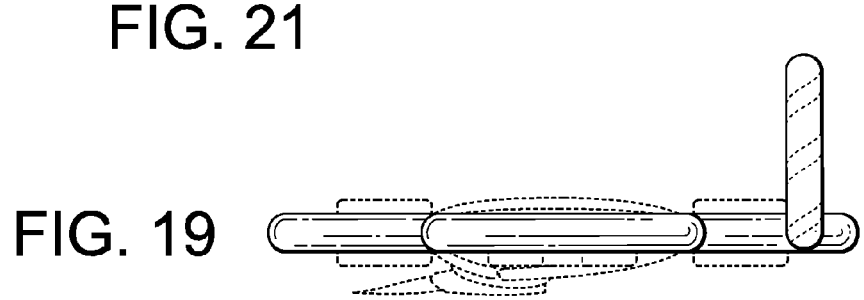
FIG. 19

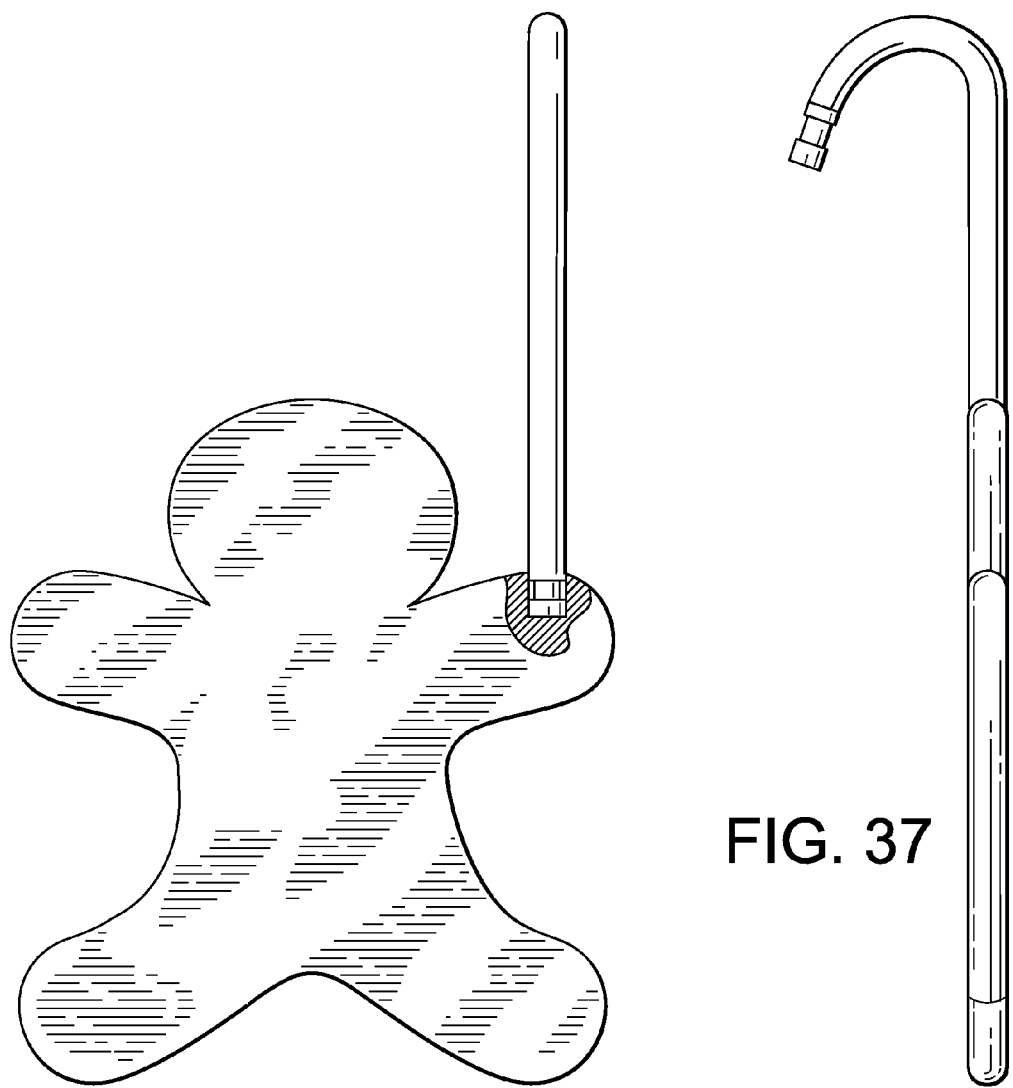
FIG. 37
FIG. 35
FIG. 33

AIR FRESHENER AND ORNAMENT

FIELD OF THE INVENTION

The present invention relates to a combined air freshener and ornament or home decoration formed of one or more polymer resin(s) loaded with a fragrance oil or oils or other fragrance material(s). The air freshener releases fragrance into the air. The air freshener converts from a self-standing holiday figure or home decoration to a tree ornament or other hanging ornament with a releasably engageable hook or support stand.

BACKGROUND OF THE INVENTION

Effective continuous action air fresheners release a sufficient amount of fragrance such that for a given enclosed space, such as a room or a motor vehicle passenger compartment, the fragrance is readily perceptible when someone enters that space. In addition effective air fresheners deliver fragrance for an acceptable period of time, such as 30 to 60 days. Moreover, such air fresheners should maintain fragrance character over this time period, such that the odor impression of the fragrance when the air freshener is activated as compared to the fragrance character at the end of the functional life is relatively the same.

Consumers may prefer portable air freshener devices that may be installed quickly and removed quickly from living spaces. Devices that may be moved from one location to another location easily also are preferred. Consumers further may prefer air freshener devices with outer configurations that more discretely fit within a living space, or configurations that add decorative flair during holiday seasons. Improvements to air freshener devices for household use continue to be sought.

Christmas tree ornaments are hung to conifer tree branches with Christmas tree hooks, ribbons, string, bands and clips, such as clips with spring-biased jaws. See, e.g., U.S. Pat. No. 6,155,526 for a hook-type hanging device. See, e.g., U.S. Pat. Nos. 4,886,688 and 7,275,727 for band-type hangers for ornaments. Improvements for ornaments and means for hanging ornaments continue to be sought.

SUMMARY OF THE INVENTION

An air freshener or air freshener and ornament combination has a body formed of a fragranced polymer that defines at least one receiving hole. A support stand is shaped so that its proximal end may be removably engaged in the receiving hole to position said body in a standing display configuration with the body supported on a substantially flat support surface, and so that its distal end may be removably engaged in the receiving hole to position said body in a hanging display configuration when the hook is engaged onto or around a support structure. The proximal end of the support stand may terminate at a first plug, and the distal end of the support stand may terminate at a second plug. Each plug may force-fit within the at least one receiving hole. In one embodiment, the support stand forms a hook or candy-cane shape with a curved portion and a straight portion.

In one particularly preferred embodiment, the air freshener includes an internal skeletal structure and the fragranced polymer forming the body is molded onto or over at least portions of the skeletal structure. The skeletal structure may be formed of metal or wire, or may be formed of a polymer such as but not limited to polypropylene and copolymers thereof. The skeletal structure may define raised portions that remain exposed after the fragranced polymer is molded onto or over the skeletal structure. Preferably the skeletal structure and, particularly, the raised portions, do not contain fragrance material. The raised portions may correspond to one or more decorations or features of the air freshener or air freshener and ornament, such as face features, clothing features, footwear features, etc.

The fragranced polymer may be any one or a mixture of polymers. Representative polymers include: polyvinylchloride, polyethylene, low density polyethylene (LDPE), high density polyethylene (HDPE), thermoplastic elastomer (TPE), polypropylene, ethylene vinyl acetate, ELVAX® EVA ethylene vinyl acetate copolymer, acetate, butyrate, propionate, silicone, copolymers thereof, and mixtures thereof. The polymer preferably is compounded, blended or mixed with one or more fragrances to form the fragranced polymer.

The support stand may be formed of a polymer, such as polypropylene and copolymers thereof. Preferably, the support stand does not contain fragrance materials.

The air freshener or air freshener and ornament may be formed into an ornamental shape. Representative, but not limiting, shapes include: gingerbread man, gingerbread woman, baby gingerbread man, gingerbread house, gingerbread cookie, Christmas cookie, Santa Claus, Mrs. Claus, reindeer, Christmas tree, snowman, snow woman, poinsettia, snowflake, and star.

DESCRIPTION OF THE FIGURES

Numerous other objects, features and advantages of the invention shall become apparent upon reading the following detailed description taken in conjunction with the accompanying drawings, in which:

FIG. 2 is a top plan view of the combined air freshener and ornament of FIG. 1;

FIG. 4 is a front elevational view of the combined air freshener and ornament of FIG. 1;

FIG. 6 is a left side elevational view of the combined air freshener and ornament of FIG. 1;

FIG. 19 is a top plan view of the combined air freshener and ornament of FIG. 18;

FIG. 21 is a front elevational view of the combined air freshener and ornament of FIG. 18;

FIG. 23 is a left side elevational view of the combined air freshener and ornament of FIG. 18;

FIG. 33 is a top plan view of the combined air freshener and ornament of FIG. 32;

FIG. 35 is a front elevational view of the combined air freshener and ornament of FIG. 32;

FIG. 37 is a left side elevational view of the combined air freshener and ornament of FIG. 32;

DESCRIPTION OF THE PREFERRED EMBODIMENTS

With reference to the drawings in which like numerals designate similar elements, a first embodiment of a combined air freshener and holiday ornament 10 is shown in FIGS. 1-14. The ornament 10 has an ornament body 12 and a hanging hook 14. The hanging hook 14 serves a dual functions of a hanging hook 14 when the ornament 10 is in a hanging configuration, such as shown in FIGS. 1-7, and as a support stand 14' when the ornament 10 is in a standing display configuration as shown in FIGS. 8-14.

Figure 8:
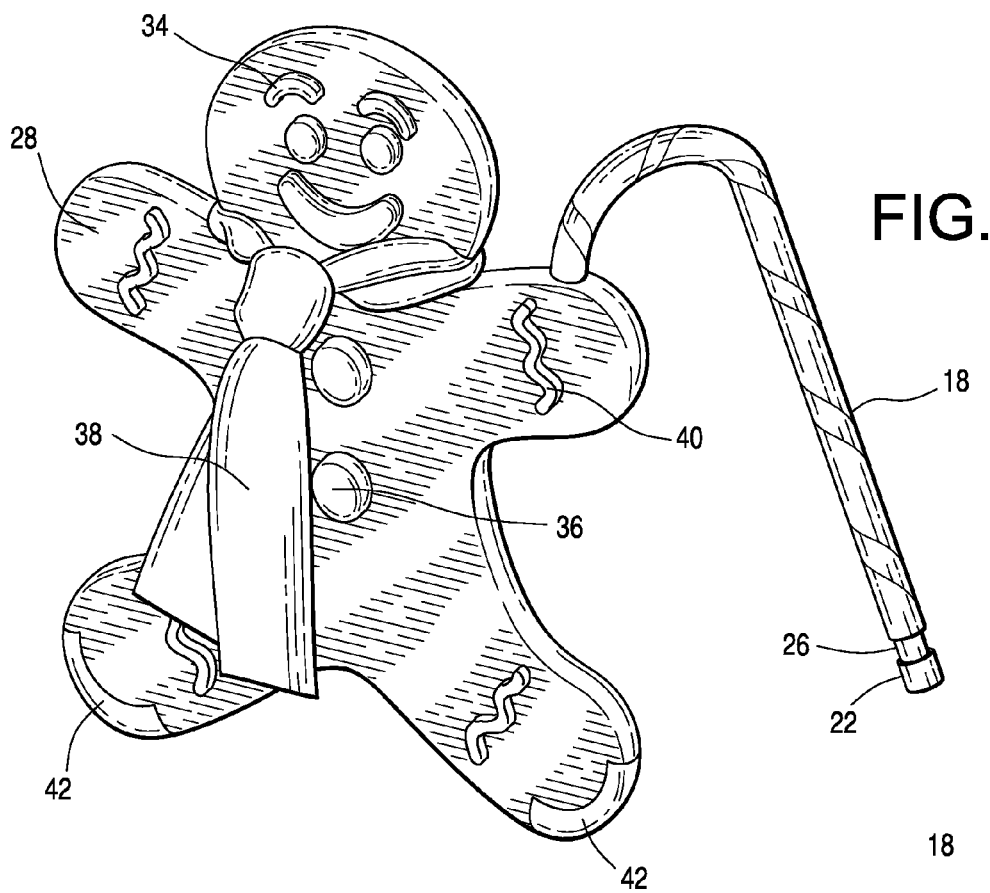
FIG. 8 is a right front perspective view of a combined air freshener and ornament in standing configuration.
Figure 10:
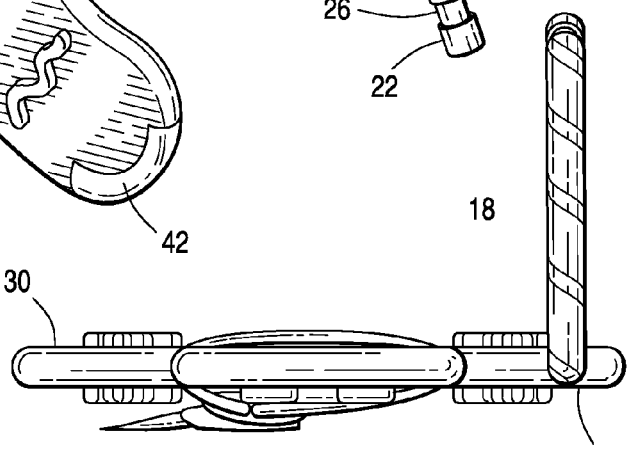
FIG. 10 is a bottom plan view of the combined air freshener and ornament of FIG. 8.
Figure 9:
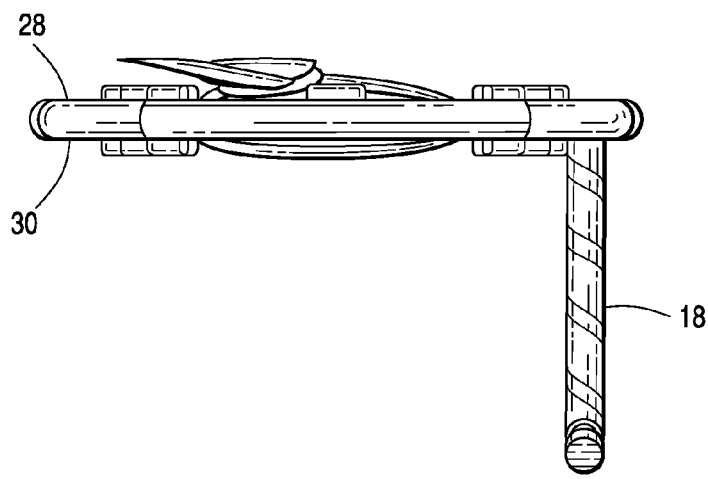
FIG. 9 is a top plan view of the combined air freshener and ornament of FIG. 8.
Figure 11:
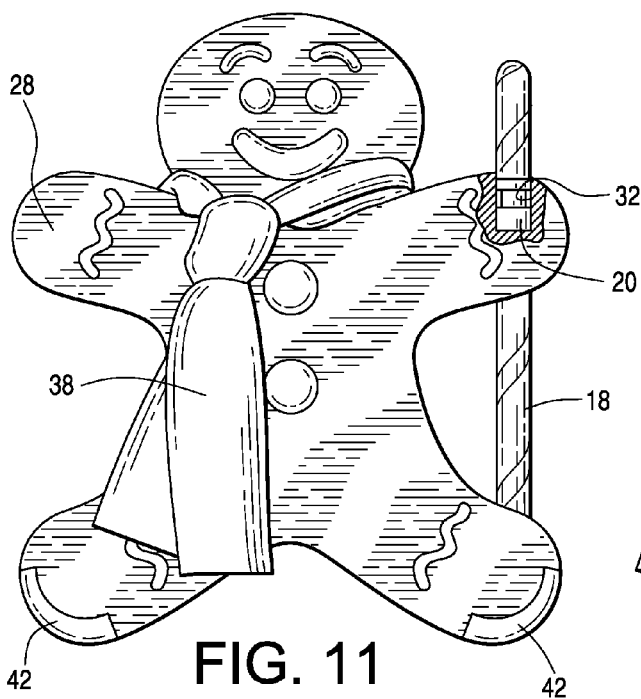
FIG. 11 is a front elevational view of the combined air freshener and ornament of FIG. 8.
Figure 13:
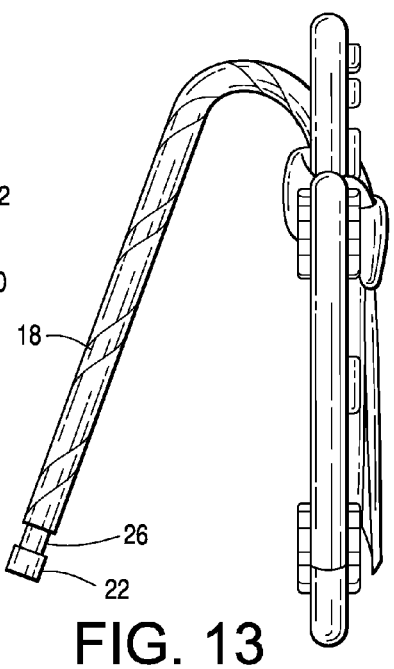
FIG. 13 is a left side elevational view of the combined air freshener and ornament of FIG. 8.
Figure 12:
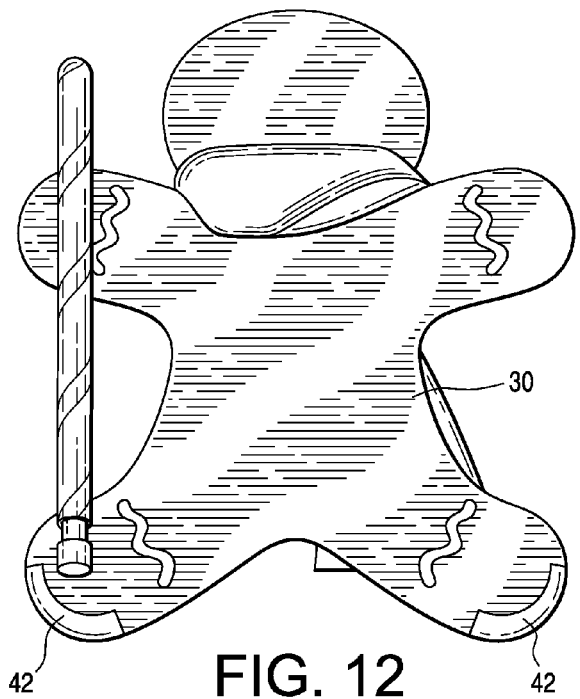
FIG. 12 is a rear elevational view of the combined air freshener and ornament of FIG. 8.
Figure 14:
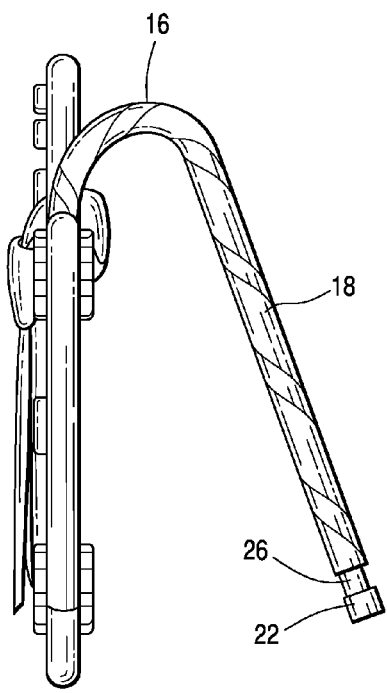
FIG. 14 is a right side elevational view of the combined air freshener and ornament of FIG. 8.

Referring to FIGS. 1-7, the hook 14 has a curved or hooked end 16 and a straight body or end 18. The hook terminates at a first plug 20 at its proximal end. The hook terminates at a second plug 22 at its distal end (FIG. 8). A first groove 24 is formed in the hook adjacent the first plug 20. A second groove 26 is formed in the hook adjacent the second plug 22 (FIG. 8).

The ornament body 12 as shown in FIGS. 1-14 has a shape or configuration of a gingerbread man or gingerbread cookie. The shape or configuration of the ornament body 12 may be any ornamental shape desired. Such shapes include, but are not limited to, gingerbread man, gingerbread woman, baby gingerbread man, gingerbread house, gingerbread cookie, Christmas cookie, Santa Claus, Mrs. Claus, reindeer, Christmas tree, snowman, snow woman, poinsettia, snowflake, star, and the like.

The support stand 14' can be configured in shapes other than a hook shape as desired. As shown in FIGS. 1-7, the support stand 14' or hook 14 is configured as a candy cane to complement the gingerbread man ornamental shape. The support stand 14' may be configured alternatively as a broom shape or bottle shape or light strand shape or other holiday-inspired ornamental shape as desired.

As shown in FIGS. 1-14, the combined air freshener and tree ornament 10 is formed of a fragranced polymer material that preferably is molded, such as by injection molding. The fragranced polymer material may comprise at least one resin selected from the group consisting of: polyvinylchlorides (PVC), polyethylenes (PE), high density polyethylenes (HDPE), low density polyethylene (LDPE), polyvinylchoride (PVC), polypropylenes, ethylene vinyl acetate copolymers (EVA), such as ELVAX® EVA ethylene vinyl acetate copolymer, thermoplastic elastomers (TPE), polypropylenes, acetate, butyrate and propionate, silicone, copolymers thereof, and mixtures thereof. The resin composition may be mixed, blended or compounded together with one or more fragrance materials and optionally with other additives known to those in the art to form an injection-moldable mixture before injection molding. A preferred amount of resin to form the air freshener/ornament is from 2 g to 100 g, more preferably 3 to 20 g.

A "fragrance material" may be any material that has a smell or odor. Most conventional fragrance materials are highly volatile essential oils. Even those which are less volatile contain highly volatile "top note" fractions which preferably are retained in the composition during processing to obtain desired fragrance power and olfactory impact by the resultant molded article. A fragrance material or a combination of fragrance materials that is compatible with the selected resin composition is preferred. The fragrance material may be a synthetically formed material or may be a naturally derived oil such as, but not limited to, the oil of Bergamot, Bitter Orange, Caraway, Cedar Leaf, Cedar Wood, Champacc, Cinnamon, Frankincense, Geranium, Lavender, Mimosa, Orange, Orignaum, Patchouli, Rosewood, Sandalwood, Vanilla, Violet, White Cedar, Ylang Ylang, Limonene, menthol, eucalyptus, camphor or the like. The particular essential oil or combination of oils to be used depends upon the particular fragrance desired for emission by the product formed.

Alternatively or additionally, the fragrance material may comprise or act as a volatile insecticide and/or insecticidal synergist or attractant or repellant, such as pyrethrum, octenol, linalool, mint oil, or a bacteriostat or pheromone. Alternatively or additionally, the fragrance material may comprise or act as a vaporous remedy for respiratory conditions, such as a vapor to relieve symptoms of colds and allergies.

Available fragrance materials are catalogued and described in references and databases known to persons skilled in the art. For example, a database is maintained by the Research Institute for Fragrance Materials at www.rifm.org. Fragrance material suppliers include Takasago International Corp. (Rockleigh, N.J.) and Symrise (Teterboro, N.J.). Exemplary synthetic fragrance materials are described in U.S. Pat. Nos. 4,411,829; 4,314,915 and 4,434,306. Preferred amounts of fragrance loading in resin are from about 5% to about 45% by weight of the resin.

Colorants (such as pigments known for use with thermoplastic and thermoset resins) may be incorporated into the polymers to improve aesthetics. Examples of suitable colorants also include any water-based colorant such as food coloring, and Reactint polymeric colorant from Milliken Chemical (Spartanburg, S.C.).

Other additives may be incorporated into the polymers as desired, including one or more plasticizers, one or more stabilizers, and optionally one or more lubricants. Decorative substances also may be entrained or mixed into the polymer(s), such as but not limited to glitter or other particles.

After molding, the fragranced polymer material forming the ornament body preferably has a hardness value (durometer) in the range of 30 to 90, preferably 60 to 70 on the Shore A scale.

Figure 1:
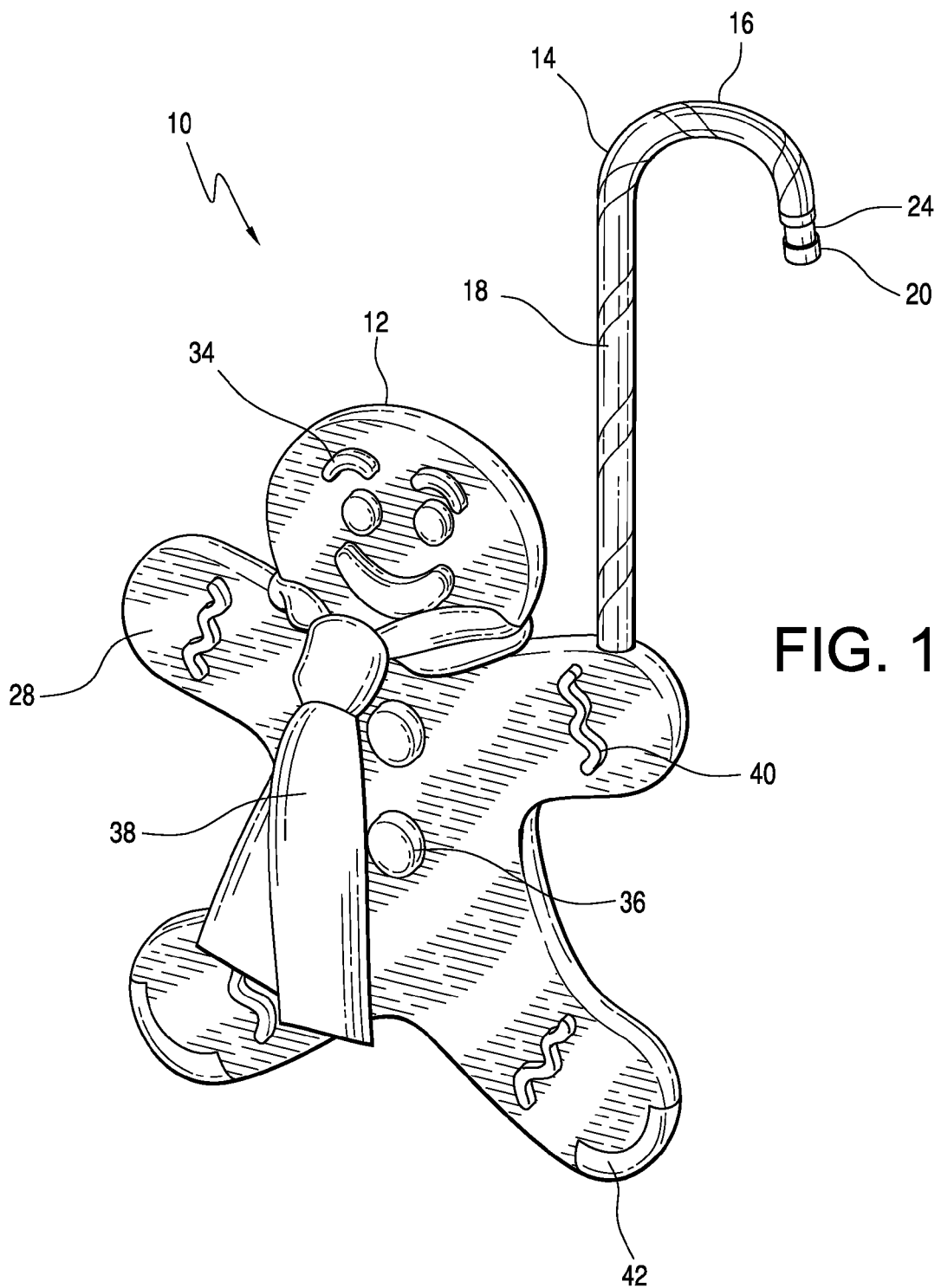
FIG. 1 is a right front perspective view of a combined air freshener and ornament in hanging configuration.
Figure 3:
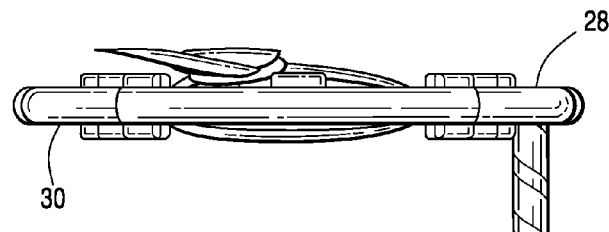
FIG. 3 is a bottom plan view of the combined air freshener and ornament of FIG. 1.
Figure 5:
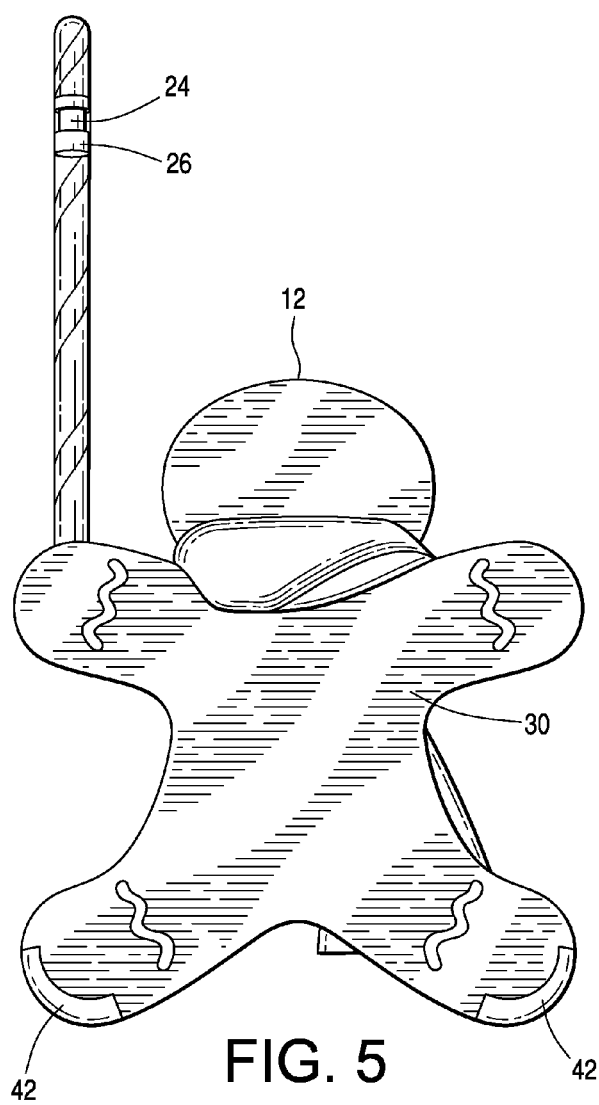
FIG. 5 is a rear elevational view of the combined air freshener and ornament of FIG. 1.
Figure 7:
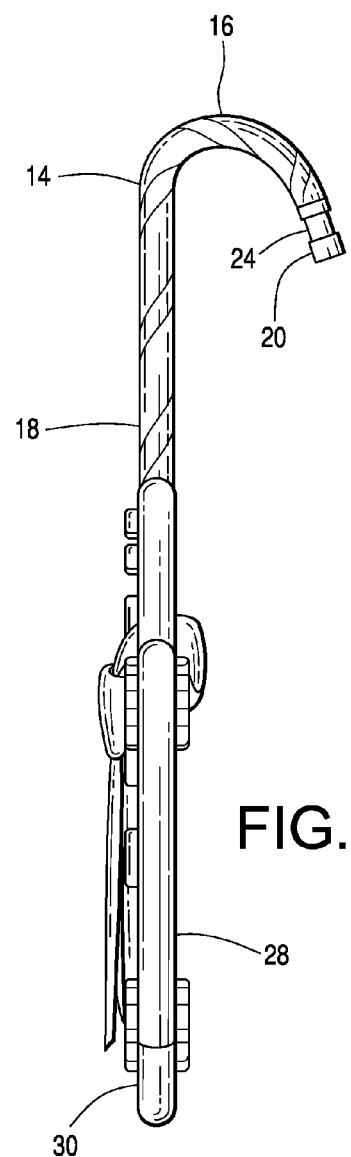
FIG. 7 is a right side elevational view of the combined air freshener and ornament of FIG. 1.

The ornament body 12 has a front face 28 and a rear face 30 opposite of the front face. The ornament body 12 may have decorative elements attached or applied thereto or co-molded therewith. Referring to FIGS. 1 and 5, face decorations 34, button decorations 36, arm decorations 40 and leg and feet decorations 42 are shown. More preferably, these decorations 34, 36, 40 and 42 may be molded together with the ornament body 12, e.g., co-injection molded. Alternatively, the ornament body 12 may be formed and the decorative elements over-molded or otherwise attached on the front face 28 and/or rear face 30, such as by adhesive.

Other types of decorative elements may be applied to the ornament body 12 as desired. In the embodiment of FIGS. 1-14, a textile ribbon or fabric is configured as a scarf or necktie 38 that is wrapped around the ornament body 12 and tied or knotted for joinder thereto. Other ribbon decorations or surface ornamentation as desired may be applied onto or around the ornament body 12.

Figure 15:
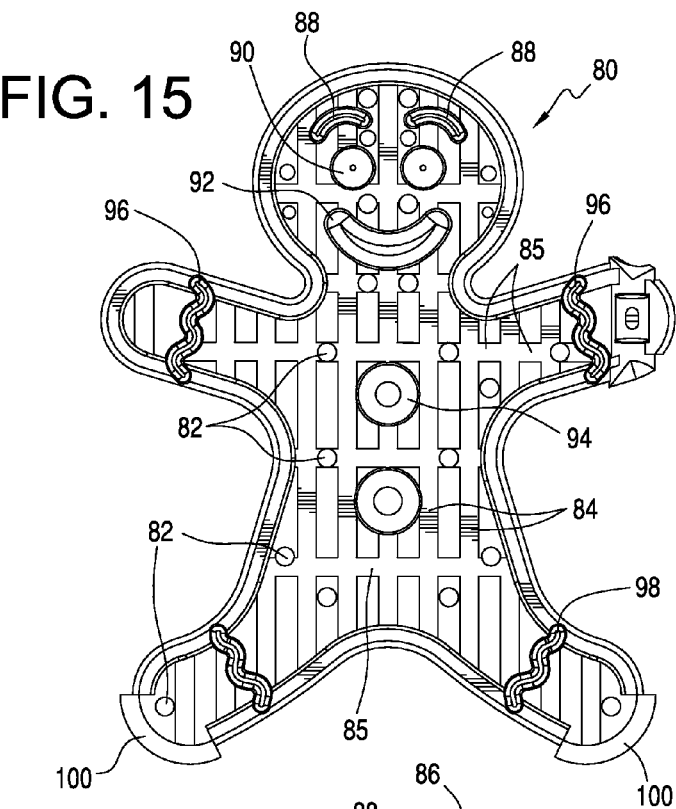
FIG. 15 is a front plan view of a skeletal structure of a combined air freshener and ornament.
Figure 16:
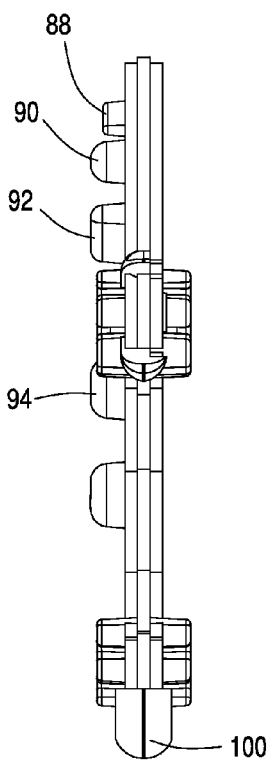
FIG. 16 is a right side elevational view of the skeletal structure of FIG. 15.
Figure 17:
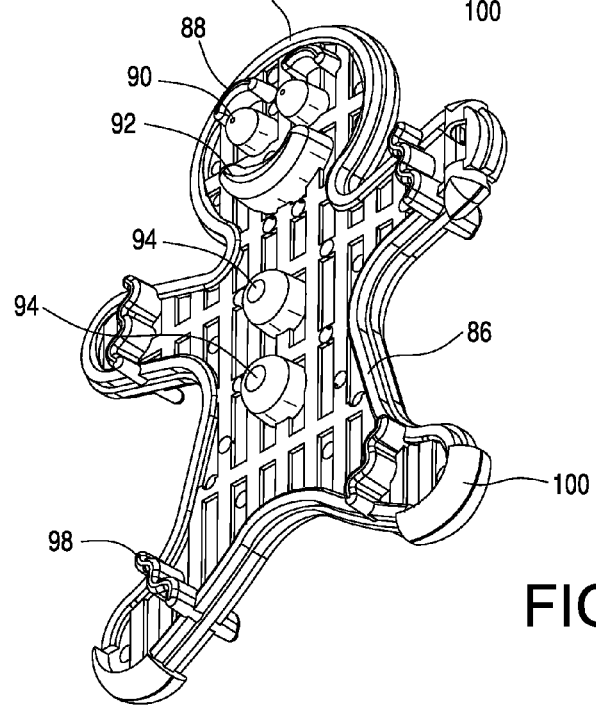
FIG. 17 is bottom right perspective view of the skeletal structure of FIG. 15.
Figure 18:
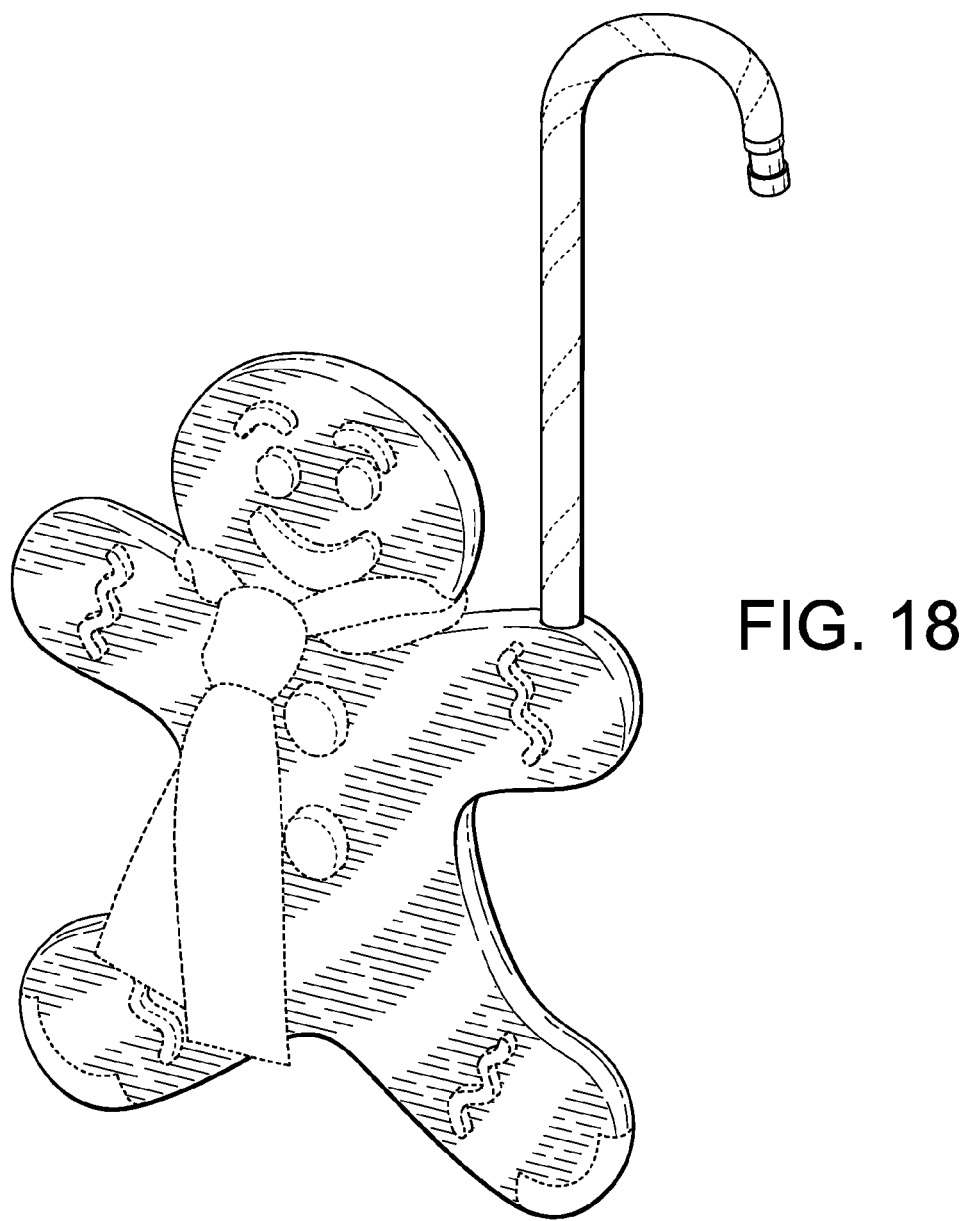
FIG. 18 is a right front perspective view of a second embodiment of a combined air freshener and ornament in hanging configuration.
Figure 20:
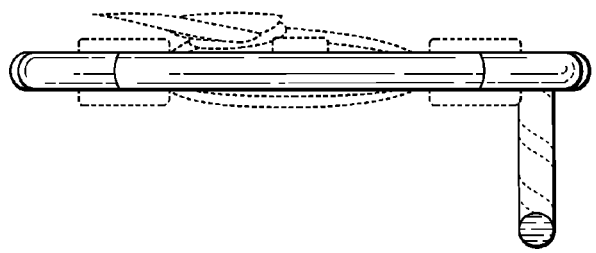
FIG. 20 is a bottom plan view of the combined air freshener and ornament of FIG. 18.
Figure 22:
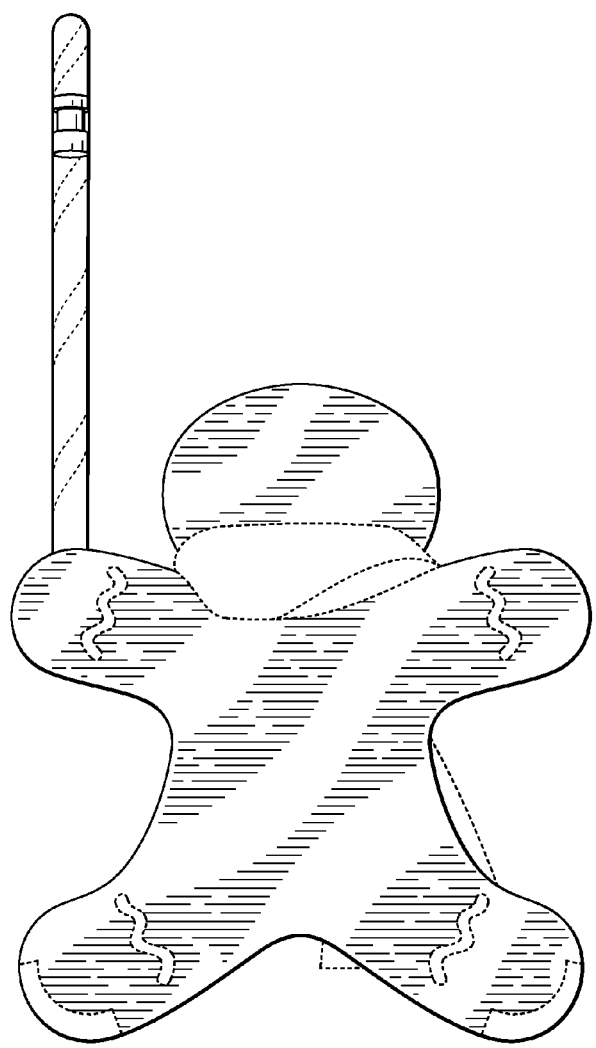
FIG. 22 is a rear elevational view of the combined air freshener and ornament of FIG. 18.
Figure 24:
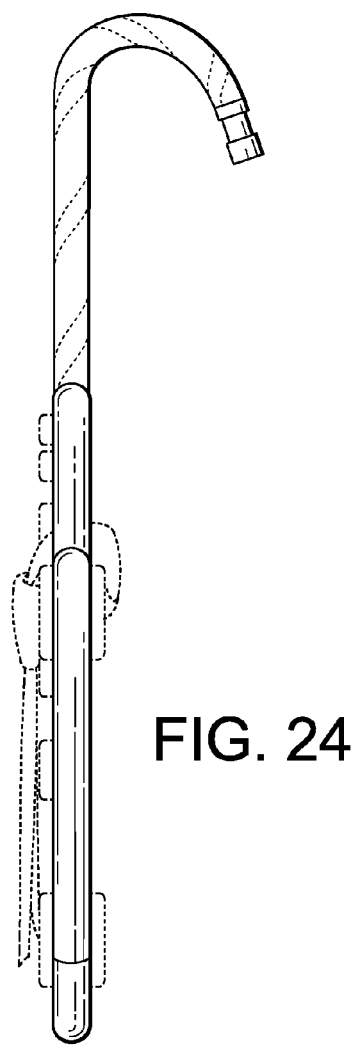
FIG. 24 is a right side elevational view of the combined air freshener and ornament of FIG. 18.
Figure 25:
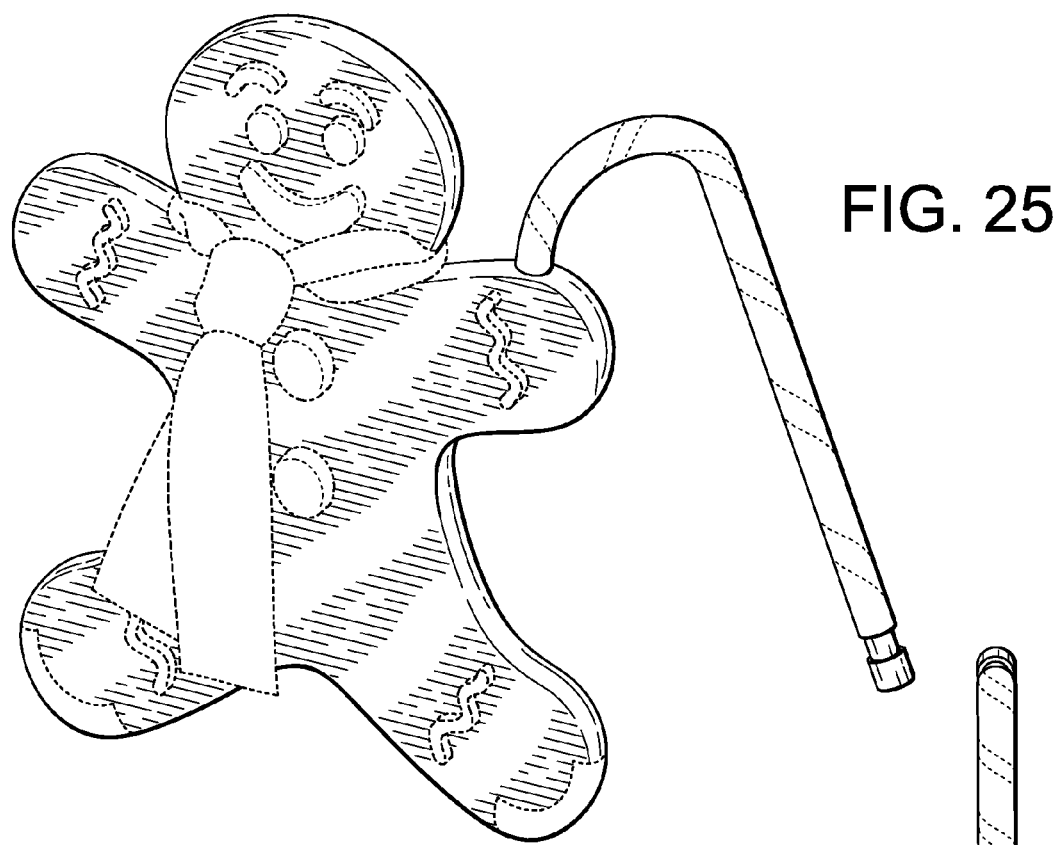
FIG. 25 is a right front perspective view of the second embodiment of a combined air freshener and ornament in standing configuration.
Figure 26:
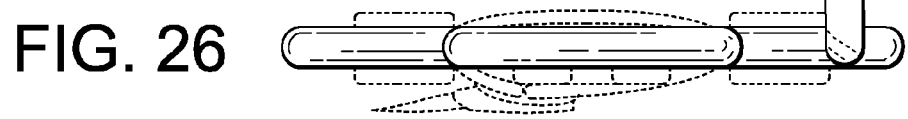
FIG. 26 is a top plan view of the combined air freshener and ornament of FIG. 25.
Figure 27:
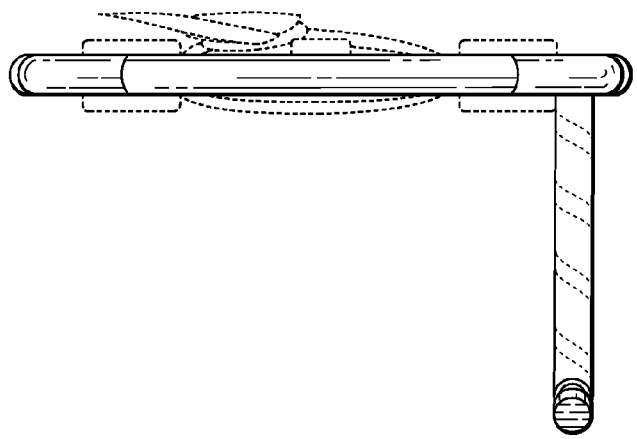
FIG. 27 is a bottom plan view of the combined air freshener and ornament of FIG. 25.
Figure 28:
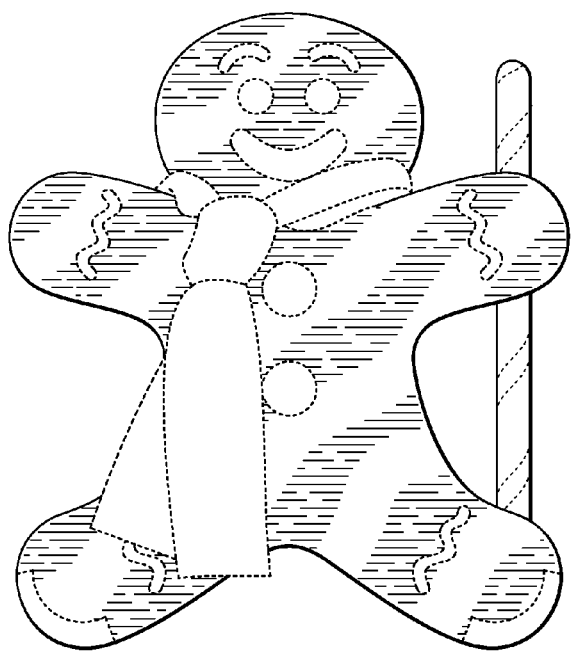
FIG. 28 is a front elevational view of the combined air freshener and ornament of FIG. 25.
Figure 30:
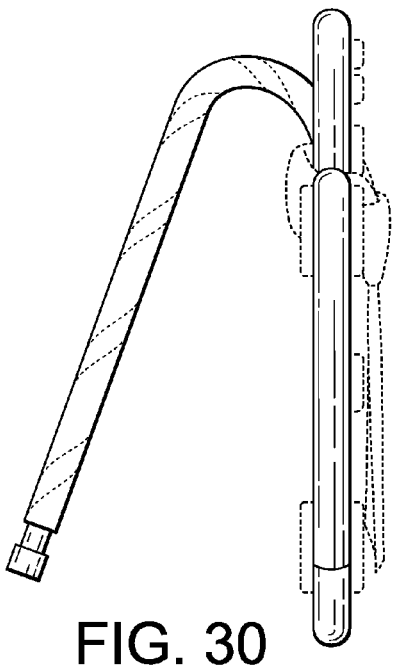
FIG. 30 is a left side elevational view of the combined air freshener and ornament of FIG. 25.
Figure 29:
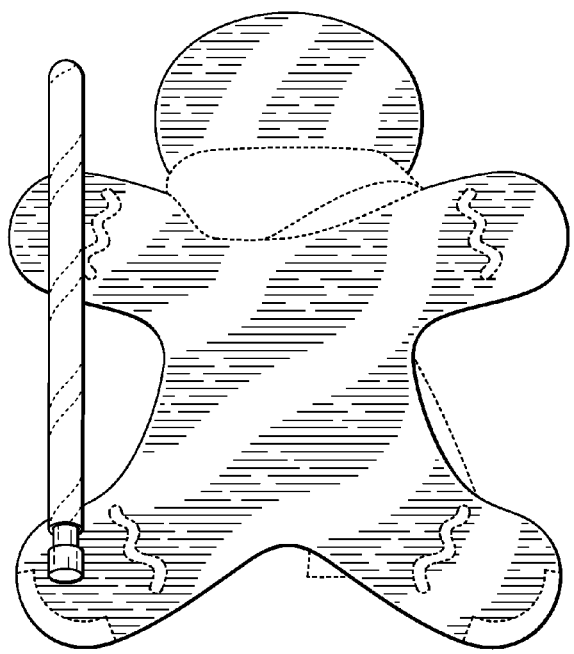
FIG. 29 is a rear elevational view of the combined air freshener and ornament of FIG. 25.
Figure 31:
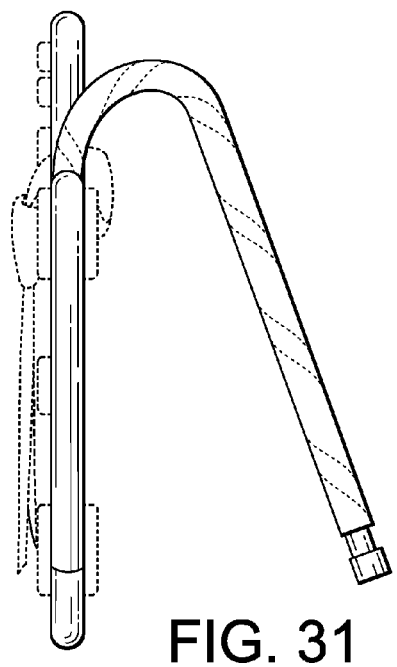
FIG. 31 is a right side elevational view of the combined air freshener and ornament of FIG. 25.

In one preferred embodiment of the invention, the fragranced polymer is over-molded onto a skeletal structure 80, such as shown in FIGS. 15-17. The skeletal structure 80 includes one or more through-holes 82 through which fragranced polymer may flow. The skeletal structure 80 has an inner network of vertical struts or rigid-enhancing portions 84 and horizontal struts or rigid-enhancing portions 85. A peripheral wall 86 defines an outer periphery for the molded body of fragranced polymer. Raised portions 88, 90, 92, 94, 96, 98 and 100 have a greater material thickness than the inner network of struts or rigid-enhancing portions 84. Upon molding fragranced polymer over or onto the skeletal structure 80, raised portions 88, 90, 92, 94, 96, 98 and 100 remain exposed to the environment without fragranced polymer material over them. Preferably, raised portions 88, 90, 92, 94, 96, 98 and 100 of the skeletal structure are formed of a polymeric material that does not incorporate fragrance. Accordingly, raised portions 88, 90, 92, 94, 96, 98 and 100 of a skeletal structure without fragrance oils do not leach or transmit fragrance oils to contacting surfaces. In this manner, the raised portions buffer the fragranced polymer from contacting household surfaces that may interact with fragrance oils in the fragranced polymer.

In this preferred embodiment, raised portions 88, 90, 92, 94, 96, 98 and 100 correspond to decorations in the finished air freshener. Raised portions 88, 90 and 92 correspond to face decorations 34. Raised portions 94 correspond to button decorations 36. Raised portions 96 correspond to arm decorations 40. Raised portions 98 correspond to leg decorations 42. In addition, raised portions 100 comprise feet decorations of the ornament/air freshener.

The raised portions 100, that may comprise feet decorations, correspond to contacting point(s) upon which the air freshener or ornament rests on a support surface when the ornament is in the standing display configuration of FIGS. 8-14.

Another advantage of the skeletal structure 80 as shown is that the through holes 82 permit the fragranced polymer forming the front portion of the ornament to integrally connect with the fragranced polymer forming the back portion of the ornament. Fragranced polymer materials tend to shrink as fragrance oils dissipate from the material. With this skeletal structure and fabrication method, the fragranced polymer material of the front and back portions of the body are chemically joined together via the through-holes, and therefore, maintain product integrity despite fragranced polymer material shrinkage.

Preferably, the skeletal structure 80 is formed of a resin, such as but not limited to, a thermoplastic elastomer including polypropylene, polyethylene, ABS, nylon, or silicone. Alternatively, the skeletal structure 80 may be configured of bent wire or molded metal.

Whether the air freshener and ornament is formed with or without a skeletal structure, the air freshener and ornament may be converted alternately as desired from a hanging configuration to a standing display configuration. The ornament body 12 defines a receiving hole or cavity or recess 32. Referring to FIGS. 1 and 8, the receiving hole 32 is formed in a top surface of one arm of the gingerbread man. The receiving hole 32 has a sufficient depth to receive either of the first plug 20 or the second plug 22 of the hanging hook 14. The receiving hole may have inwardly tapered walls to improve the force fit between the plug 20 or 22 and the receiving hole 32. Preferably, the receiving hole 32 has a circular circumference and the first and second plugs 20, 22 have round exteriors to mate within the receiving hole 32. As shown in FIG. 1 in the hanging configuration, the second plug 22 seats within the receiving hole 32 to a depth such that the second plug 22 and the groove 26 are held within the receiving hole 32. As shown in FIG. 8, in the alternative standing display configuration, the first plug 20 seats within the receiving hole 32 to a depth such that the first plug 20 and the groove 24 are held within the receiving hole 32 to a depth such that the first plug 20 and groove 24 are held within the receiving hole 32.

When in the hanging configuration, as shown in FIGS. 1-7, the air freshener and ornament 10 may be suspended for display by joining the hooked portion 16 of the hanging hook 14 to a supporting structure, such as a Christmas tree bough or branch. When in the standing display configuration, as shown in FIGS. 8-14, the air freshener and ornament 10 may be supported above a supporting surface, such as a table, or desk or window ledge, etc. The leg or feet portions of the ornament 10 and the distal end or plug 22 of the hanging hook 14 contact the supporting surface to hold the air freshener and ornament 10 in a generally upright standing position.

Most preferably, the foot decoration 42 or 100 is formed of a polymer material that does not include fragrance oil so that when the foot decoration 42 or 100 contacts a support surface it does not mar such support surface with fragrance oil. Most preferably, the decorations 34, 36, 40 or the raised portions 88, 90, 92, 94, 96, 98 and 100 are formed of a polymer material that does not include fragrance oil so that when these decorations or raised portions contact other surfaces, they do not mar such surfaces with fragrance oil.

The invention has been illustrated with particular reference to attaching or engaging the combined air freshener and ornament 10 to tree bough or branch. The combined air freshener and ornament 10 may be useful in alternative environments of use, such as attached or clipped to curtain rods in closets or cabinets, or to motor vehicle door handles, curtain rods, closet rods, hangers, shelving, shelving support posts, drawer pulls, drawer handles, belt loops, shoes, shoe racks, hampers, gym bags, lockers, shower doors, towel racks, trash cans, pipes, wires, tables, and carts, and is not intended to be limited to the environment of use illustrated here.

Alternatively, the combined air freshener and ornament according to the invention may be installed on a belt or on a belt loop or other clothing item and worn as a personal air freshening device. Such embodiment has particular appeal where the fragrance material comprises a volatile insecticide, or where the fragrance material comprises a cold or allergy vapor remedy.

Referring to FIGS. 18-31, the air freshener and ornament according to the invention 10 is shown with ornamental features, such as face decoration 34, button decoration 36, necktie decoration 38, arm decoration 40, leg decoration 42, disclaimed by phantom lines.

Figure 32:
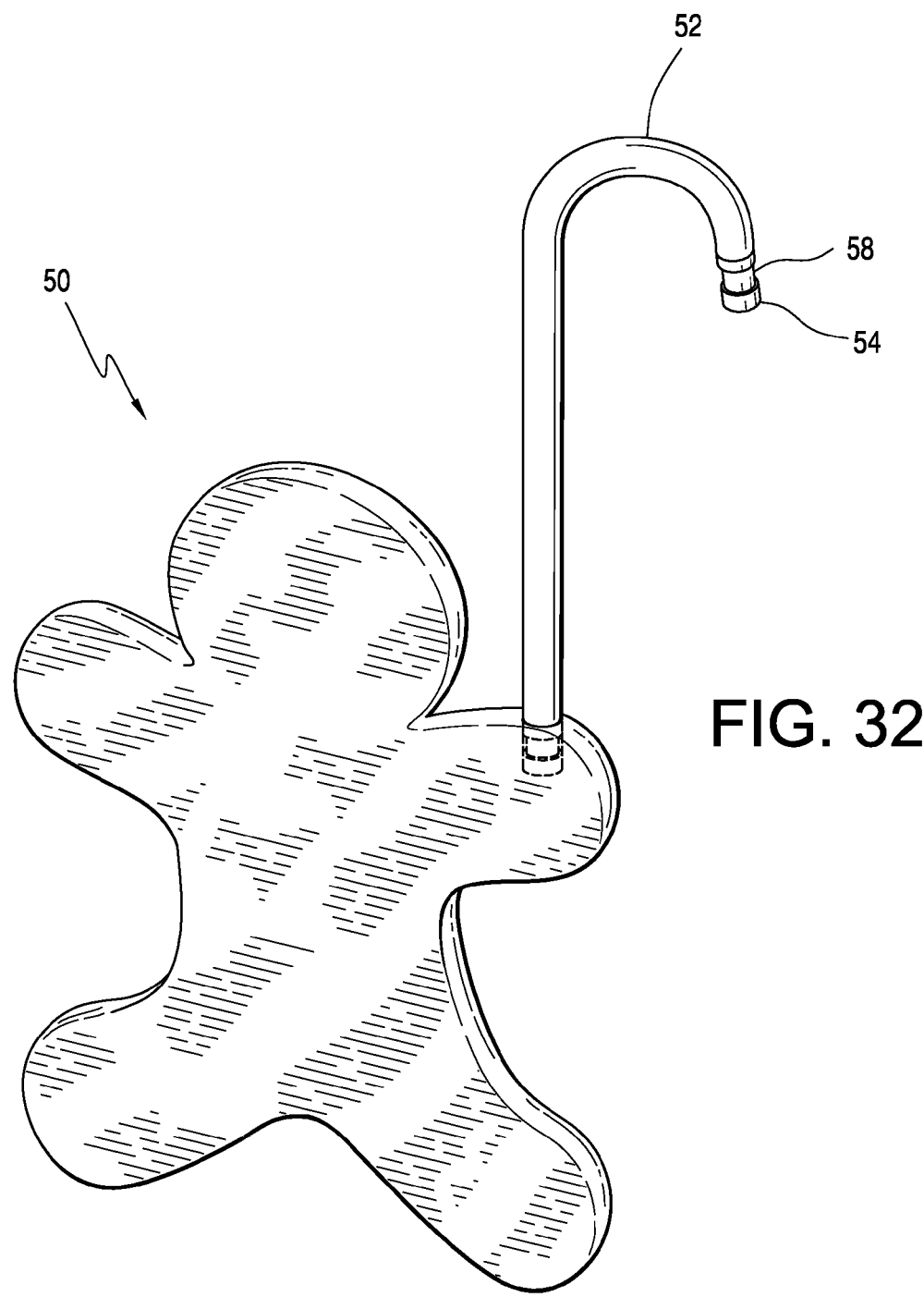
FIG. 32 is a right front perspective view of a third embodiment of a combined air freshener and ornament in hanging configuration.
Figure 34:
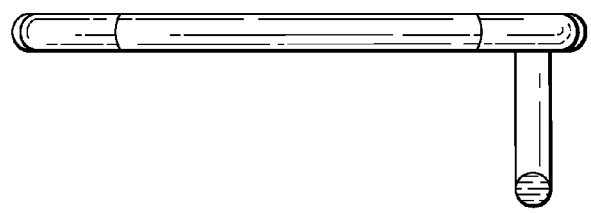
FIG. 34 is a bottom plan view of the combined air freshener and ornament of FIG. 32.
Figure 36:
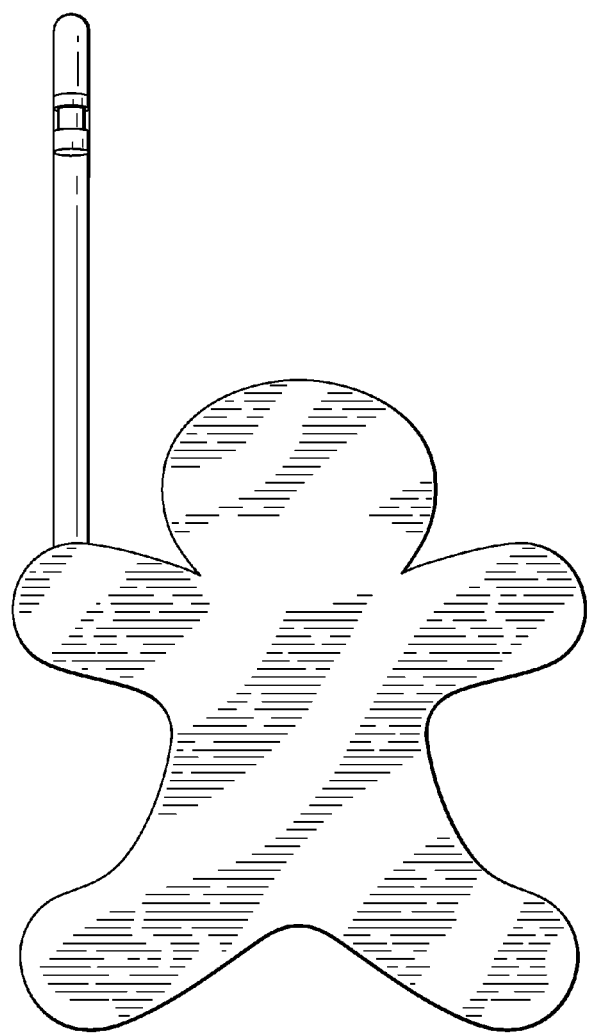
FIG. 36 is a rear elevational view of the combined air freshener and ornament of FIG. 32.
Figure 38:
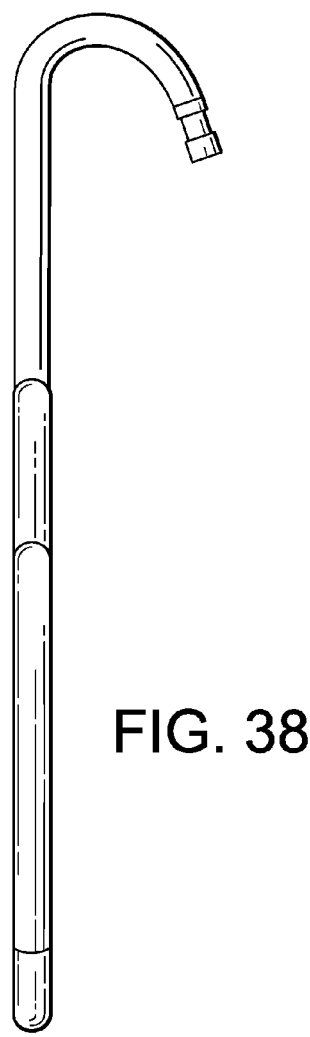
FIG. 38 is a right side elevational view of the combined air freshener and ornament of FIG. 32.
Figure 39:
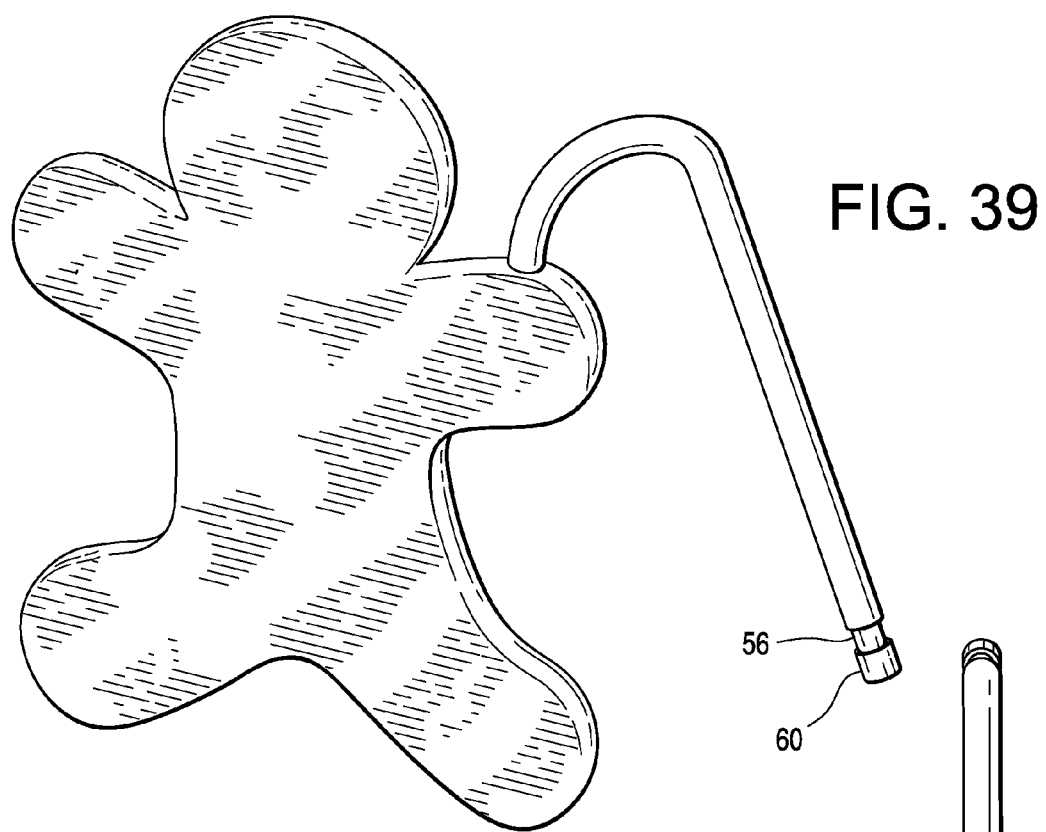
FIG. 39 is a right front perspective view of the third embodiment of the combined air freshener and ornament in standing configuration.
Figure 40:
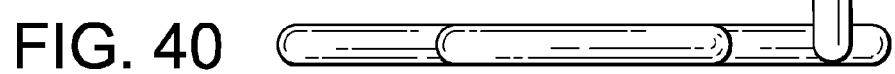
FIG. 40 is a top plan view of the combined air freshener and ornament of FIG. 39.
Figure 41:
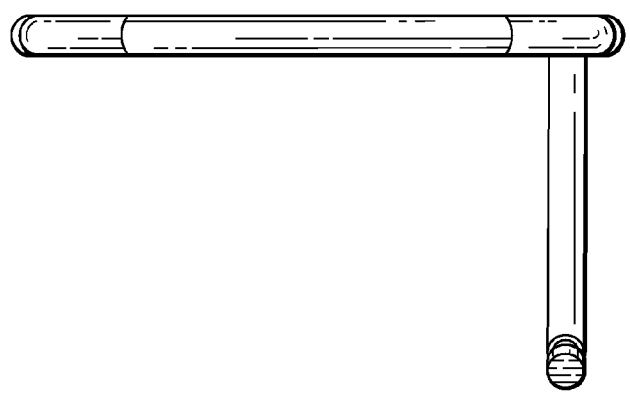
FIG. 41 is a bottom plan view of the combined air freshener and ornament of FIG. 39.
Figure 42:
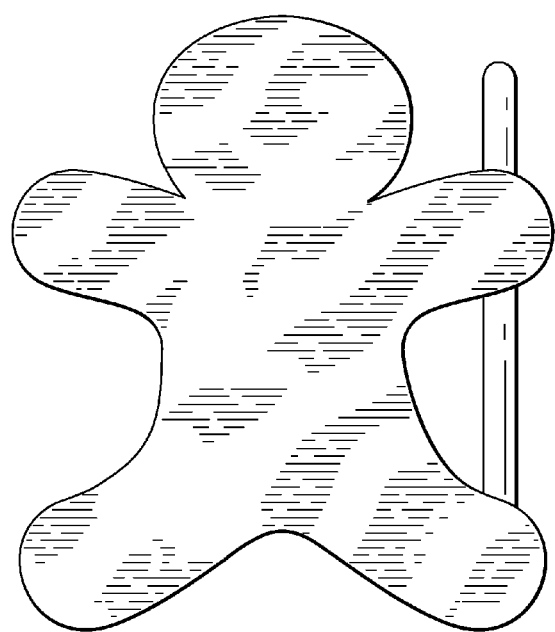
FIG. 42 is a front elevational view of the combined air freshener and ornament of FIG. 39.
Figure 44:
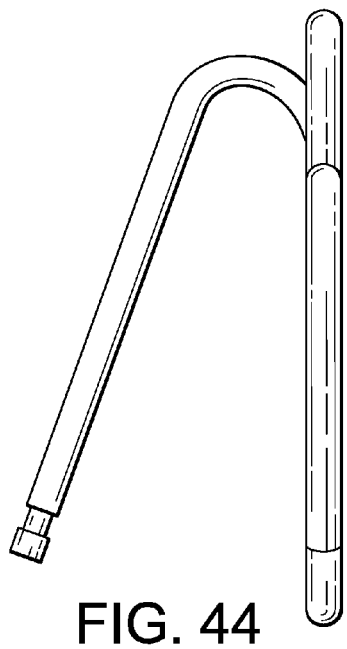
FIG. 44 is a left side elevational view of the combined air freshener and ornament of FIG. 39.
Figure 43:
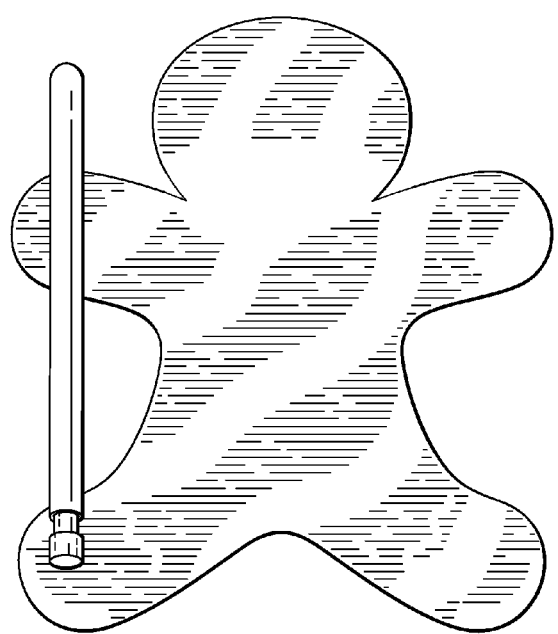
FIG. 43 is a rear elevational view of the combined air freshener and ornament of FIG. 39.
Figure 45:
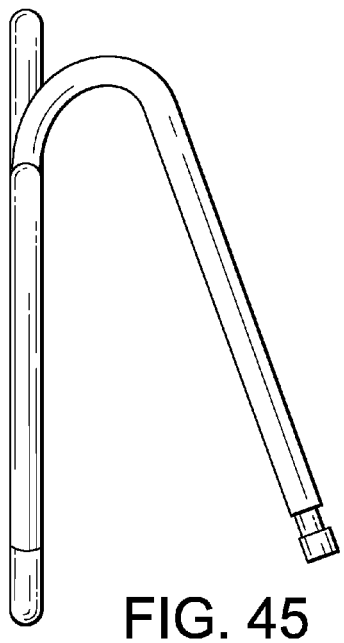
FIG. 45 is a right side elevational view of the combined air freshener and ornament of FIG. 39.

Referring next to FIGS. 32-45, an alternative embodiment 50 of the air freshener and ornament according to the invention is shown without surface decoration. A hanging hook 52 comprises a cane-like shape with a hooked or curved end and a straight end. The hooked end terminates in a proximal plug end 54, with a groove 58 adjacent thereto. The straight end terminates in a distal plug end 56, with a groove 60 adjacent thereto. The alternative embodiment adjusts from a hanging display configuration as shown in FIGS. 32-38 to a standing display configuration as shown in FIGS. 39-45 in the same manner as the first embodiment. The hanging hook 52 may be joined by the distal knob or plug end 56 to a receiving hole in the air freshener and ornament 50 for the hanging hook to serve as a hanging means in the hanging display configuration (FIG. 32). The hanging hook 52 alternatively may be joined by the proximal knob or plug 54 to the receiving hole in the air freshener and ornament 50 for the hanging hook to support the ornament 50 in its standing display configuration (FIG. 39).

Air fresheners may be tested for fragrance character and fragrance strength using a fragrance panel test known in the fragrance industry. A sample air freshener product is suspended in a room with dimensions of 25 feet by 16 feet by 9 feet. A panel of at least four persons ranks the strength and character of the aroma emitted by the various air freshener products on a scale of 0 to 5, with 5 being the strongest and 5 being the closest in character to the fragrance oil. The fragrance power and fragrance character are observed over a four-week period. The fragrance power values are averaged, and the fragrance character values are averaged. Products that receive average rankings of 3 and above for the entire testing period are satisfactory for use as continuous action room air fresheners.

Air fresheners may be tested for suitability and durability for use as air fresheners. For example, the air fresheners may be frozen for at least 12 hours and thawed over a repeated number of cycles (such as 3 cycles) to determine whether fragrance material exudes from the polymer upon thawing. Air fresheners may be heated to an elevated temperature of at least 120° F. and held for 4 weeks at such temperature, in packaging and outside of packaging, to determine whether fragrance exudes and whether fragrance strength and fragrance character degrade. Air fresheners may be exposed to ultraviolet light testing for at least 4 weeks to determine effect of light on product color and fragrance character.

While preferred embodiments of the invention have been described and illustrated here, various changes, substitutions and modifications to the described embodiments will become apparent to those of ordinary skill in the art without thereby departing from the scope and spirit of the invention.

What is claimed is:

1. An air freshener, comprising:
   a body defining at least one receiving hole, said body formed of a fragranced polymer;
   a hook having a curved portion and a straight portion, with the curved portion terminating at a proximal end and the straight portion terminating at a distal end, wherein the proximal end of the hook terminates at a first plug and the distal end of the hook terminates at a second plug;
   wherein said proximal end is adapted to removably engage the receiving hole to position said body in a standing display configuration with the body supported on a substantially flat support surface with the distal end of the hook in contact with the support surface in the standing display configuration; and
   wherein said distal end is adapted to removably engage the receiving hole to position said body in a hanging display configuration when the hook is engaged onto or around a support structure from which the air freshener is suspended in the hanging display configuration.

2. The air freshener of claim 1, further comprising a skeletal structure, and wherein the fragranced polymer forming the body is molded onto or over at least portions of the skeletal structure.

3. The air freshener of claim 2, wherein the body is overmolded over the skeletal structure.

4. The air freshener of claim 2, wherein the skeletal structure defines raised portions, and said raised portions remain exposed after the fragranced polymer of the body is molded onto or over the skeletal structure.

5. The air freshener of claim 4, wherein said raised portions correspond to one or more decorations.

6. The air freshener of claim 1, wherein the fragranced polymer is formed of a polymer selected from the group consisting of: polyvinylchloride, polyethylene, low density polyethylene (LDPE), high density polyethylene (HDPE), thermoplastic elastomer (TPE), polypropylene, ethylene vinyl acetate, ethylene vinyl acetate copolymer, acetate, butyrate, propionate, silicone, copolymers thereof, and mixtures thereof.

7. The air freshener of claim 6, wherein the polymer is compounded, blended or mixed with one or more fragrances to form the fragranced polymer.

8. The air freshener of claim 2, wherein the skeletal structure is formed of a polymer selected from the group consisting of: polypropylene, polyethylene, acrylonitrile butadiene styrene, nylon, silicone, and copolymers thereof.

9. The air freshener of claim 1, wherein the ornament body is formed into a shape selected from the group consisting of: gingerbread man, gingerbread woman, baby gingerbread man, gingerbread house, gingerbread cookie, Christmas cookie, Santa Claus, Mrs. Claus, reindeer, Christmas tree, snowman, snow woman, poinsettia, snowflake, and star.

10. An air freshener, comprising:
- a body comprising a skeletal structure defining raised portions onto or over which is molded a fragranced polymer, wherein said raised portions remain exposed after the fragranced polymer of the body is molded onto or over the skeletal structure, said body defining at least one receiving hole;
- a support stand with a proximal end and a distal end;
- wherein said proximal end is adapted to removably engage the receiving hole to position said body in a standing display configuration with the body supported on a substantially flat support surface with the distal end of the support stand in contact with the support surface in the standing display configuration, and with at least a portion of said raised portions of the body corresponding to one or more feet or surface-contacting supports for supporting the air freshener on the substantially flat support surface when in the standing display configuration; and
- wherein said distal end is adapted to removably engage the receiving hole to position said body in a hanging display configuration when the support stand is engaged onto or around a support structure from which the air freshener is suspended in the hanging display configuration.

11. The air freshener of claim 10, wherein the body is over molded over the skeletal structure.

12. The air freshener of claim 10, wherein at least a portion of said raised portions correspond to one or more decorations.

13. The air freshener of claim 10, wherein the fragranced polymer is formed of a polymer selected from the group consisting of: polyvinylchloride, polyethylene, low density polyethylene (LDPE), high density polyethylene (HDPE), thermoplastic elastomer (TPE), polypropylene, ethylene vinyl acetate, ethylene vinyl acetate copolymer, acetate, butyrate, propionate, silicone, copolymers thereof, and mixtures thereof.

14. The air freshener of claim 13, wherein the polymer is compounded, blended or mixed with one or more fragrances to form the fragranced polymer.

15. The air freshener of claim 10, wherein the skeletal structure is formed of a polymer selected from the group consisting of polypropylene, polyethylene, acrylonitrile butadiene styrene, nylon, silicone, and copolymers thereof.

* * * * *